United States Patent
Mashinchian et al.

(10) Patent No.: US 11,413,316 B2
(45) Date of Patent: Aug. 16, 2022

(54) IN VITRO PRODUCTION OF MUSCLE STEM CELLS

(71) Applicant: NESTEC S.A., Vevey (CH)

(72) Inventors: Omid Mashinchian, Lausanne (CH); Jerome Feige, Crissier (CH); Conrad Florian Bentzinger, Sherbrooke (CA)

(73) Assignee: Societe des Produits Nestle S.A., Vevey (CH)

( * ) Notice: Subject to any disclaimer, the term of this patent is extended or adjusted under 35 U.S.C. 154(b) by 482 days.

(21) Appl. No.: 16/461,595

(22) PCT Filed: Nov. 3, 2017

(86) PCT No.: PCT/EP2017/078119
§ 371 (c)(1),
(2) Date: May 16, 2019

(87) PCT Pub. No.: WO2018/091282
PCT Pub. Date: May 24, 2018

(65) Prior Publication Data
US 2019/0365821 A1 Dec. 5, 2019

(30) Foreign Application Priority Data
Nov. 18, 2016 (EP) .................................. 16199441

(51) Int. Cl.
*A61K 35/34* (2015.01)
*A61K 35/44* (2015.01)
*A61K 35/545* (2015.01)
*C12N 5/071* (2010.01)

(52) U.S. Cl.
CPC .............. *A61K 35/34* (2013.01); *A61K 35/44* (2013.01); *A61K 35/545* (2013.01); *C12N 5/0697* (2013.01); *C12N 2501/727* (2013.01); *C12N 2502/1323* (2013.01); *C12N 2502/28* (2013.01); *C12N 2502/45* (2013.01); *C12N 2513/00* (2013.01)

(58) Field of Classification Search
CPC ....... A61K 35/34; A61K 35/44; A61K 35/545
See application file for complete search history.

(56) References Cited

FOREIGN PATENT DOCUMENTS

| EP | 1437406 | 7/2004 |
|---|---|---|
| WO | 2007059612 | 5/2007 |

OTHER PUBLICATIONS

Orlidge et al., "Inhibition of Capillary Endothelial Cell Growth by Pericytes and Smooth Muscle Cells", The Journal of Cell Biology, 1987, vol. 105, pp. 1455-1462. (Year: 1987).*
Hosoyama et al. "Derivation of Myogenic Progenitors Directly From Human Pluripotent Stem Cells Using a Sphere-Based Culture" Stem Cells Translational Medicine, 2014, vol. 3, pp. 564-574.
Kuang et al. "Asymmetric Self-Renewal and Commitment of Satellite Stem Cells in Muscle" Cell, 2007, vol. 129, pp. 999-1010.
Roca et al. "Myogenic Precursors from iPS Cells for Skeletal Muscle Cell Replacement Therapy" Journal of Clinical Medicine, 2015, vol. 4, pp. 243-259.
Yin et al. "Engineering Stem Cell Organoids" Cell Stem Cell, 2016, vol. 18, pp. 25-38.
Yin et al. "Satellite Cells and the Muscle Stem Cell Niche" Physiol Rev, 2013, vol. 93, pp. 23-67.
Hosseinkhani et al. "Engineering of the Embryonic and Adult Stem Cell Niches" Iran Red Crescent Med J, 2013, vol. 2, pp. 83-92.
Mizuno et al. "Generation of skeletal muscle stem / progenitor cells from murine induced pluripotent stem cells" Faseb J, 2010, vol. 24, pp. 2245-2253.
Pannerec et al. "Stem cells in the hood: the skeletal muscle niche" Trends in Molecular Medicine, 2012, vol. 18, No. 10, pp. 599-606.

* cited by examiner

*Primary Examiner* — Laura Schuberg
(74) *Attorney, Agent, or Firm* — K&L Gates LLP

(57) ABSTRACT

An in vitro method of producing a population of muscle stem cells comprising co-culturing pluripotent stem cells, embryonic fibroblast cells and endothelial cells in 3D cell culture.

16 Claims, 11 Drawing Sheets

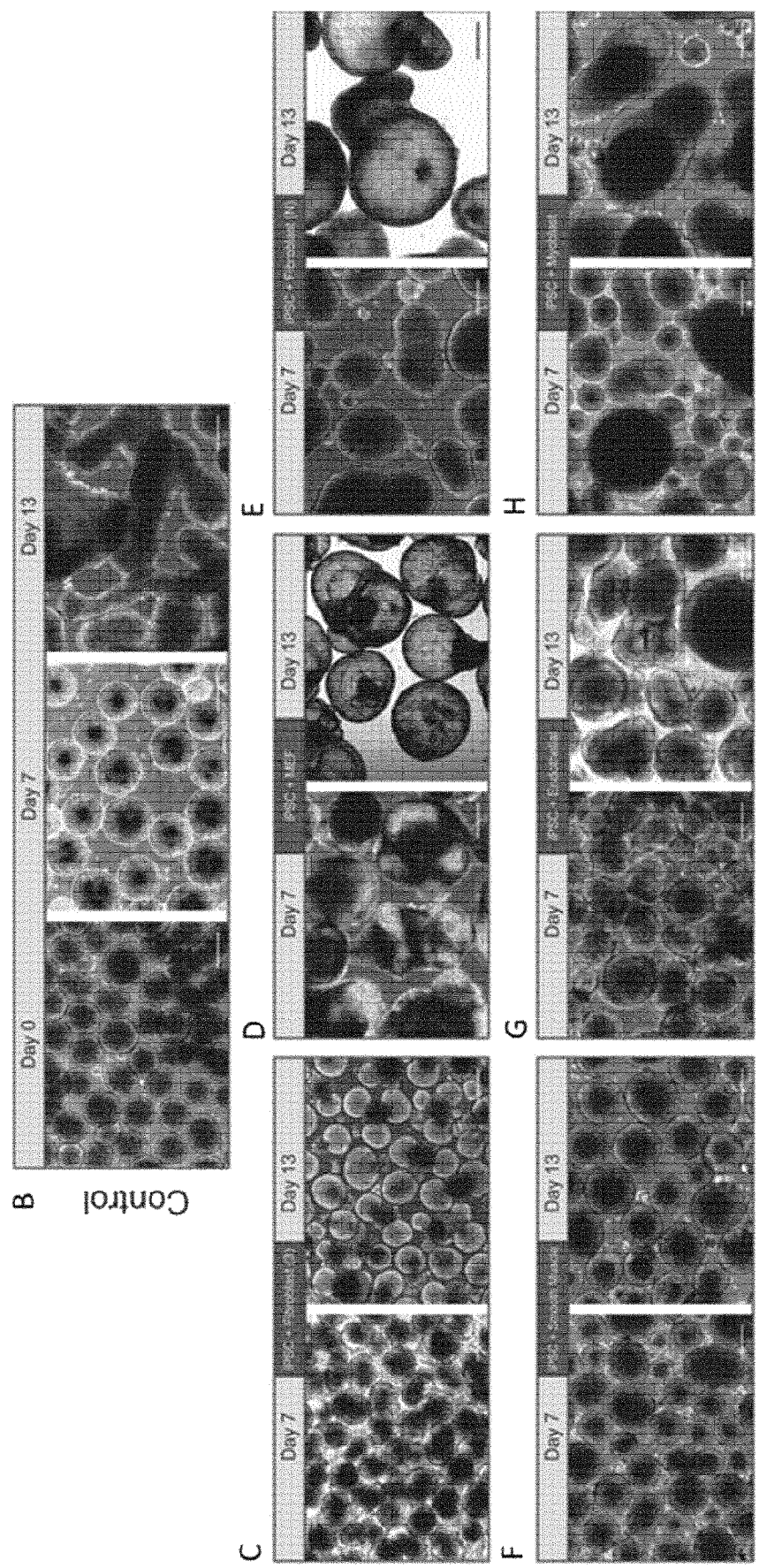
Figure 3 — cont'd

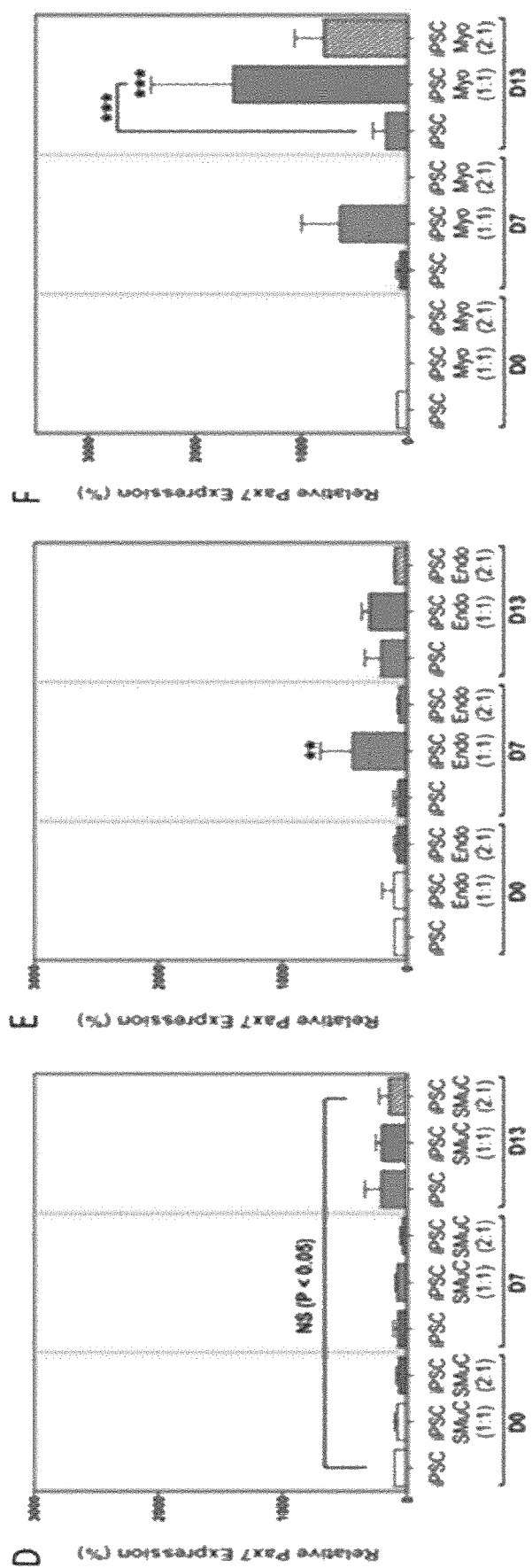
Figure 4-cont'd

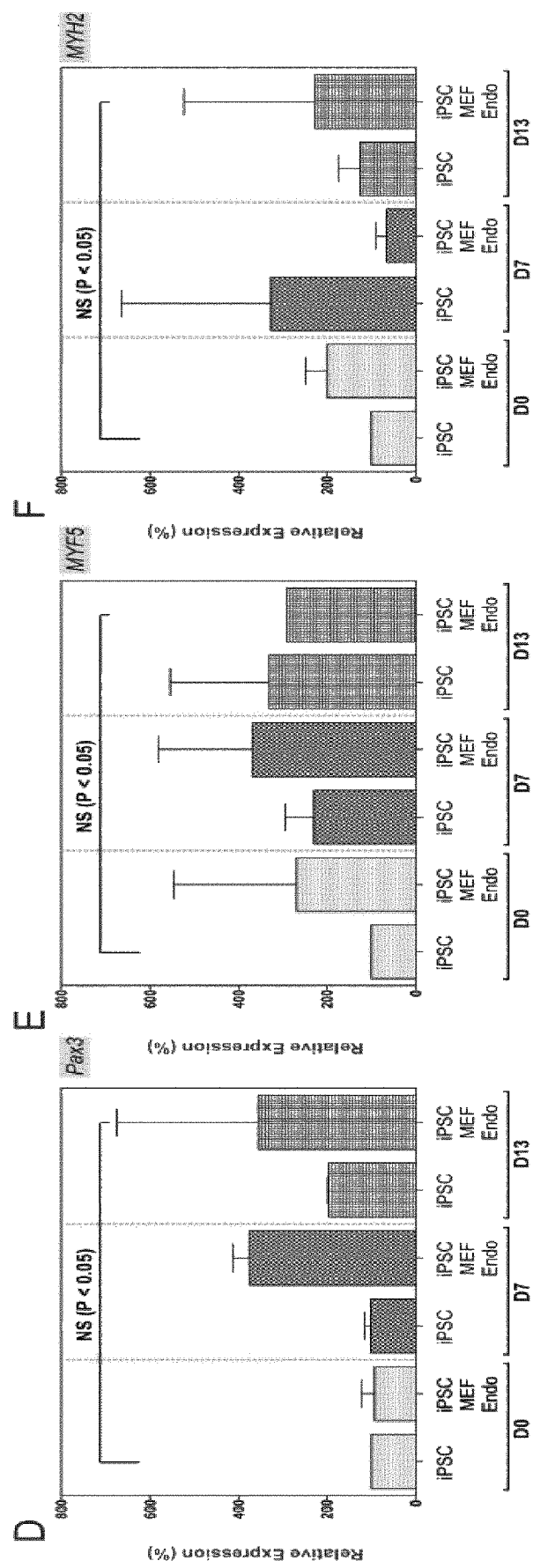
Figure 5- cont'd

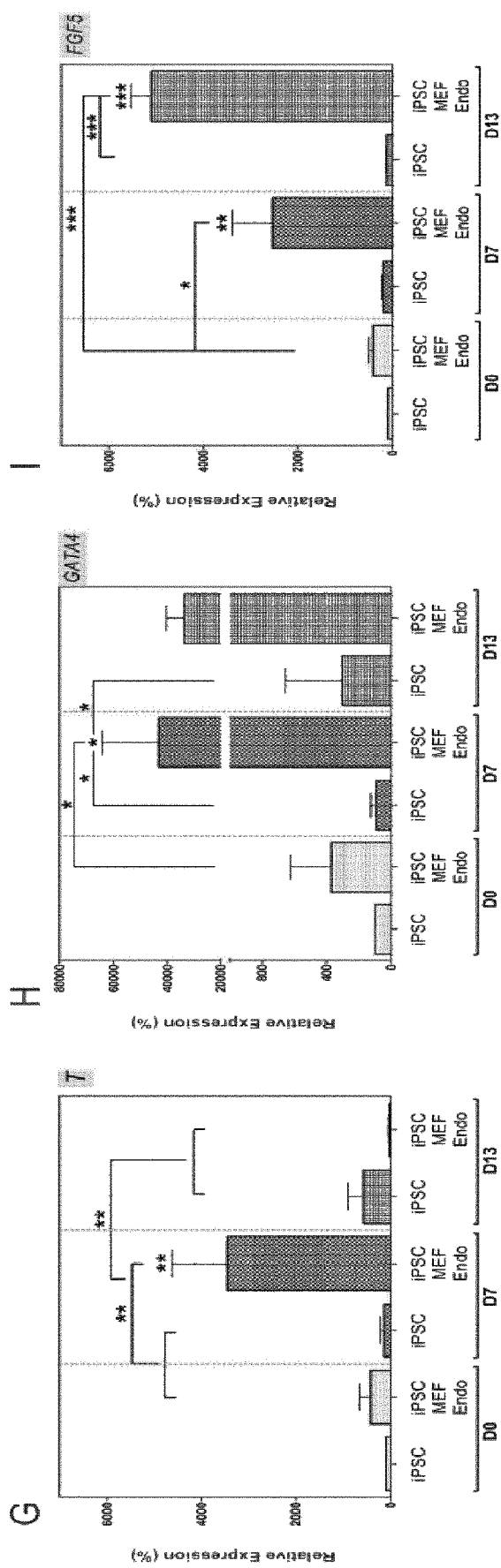
Figure 5- cont'd

IN VITRO PRODUCTION OF MUSCLE STEM CELLS

CROSS REFERENCE TO RELATED APPLICATIONS

The present application is a National Stage of International Application No. PCT/EP2017/078119, filed on Nov. 3, 2017, which claims priority to European Patent Application No. 16199441.3, filed on Nov. 18, 2016, the entire contents of which are being incorporated herein by reference.

FIELD OF THE INVENTION

The present invention relates to in vitro methods of producing muscle stem cells, in particular, skeletal muscle stem cells that are uncommitted and maintain their long-term engraftment potential. The invention also relates to muscle stem cells produced by such methods, and the use of the muscle stem cells in therapy and in methods of screening for agents capable of increasing their self-renewal, proliferation or differentiation.

BACKGROUND TO THE INVENTION

Muscle atrophy, a partial or complete wasting of the muscle, can be experienced by subjects who suffer temporary disabling circumstances. However, muscle atrophy is also a consequence of a number of muscle-wasting disorders, such as myopathy, muscular dystrophy and sarcopenia.

Muscular dystrophy is a group of disorders that result in the weakening and breakdown of skeletal muscles. This group comprises 9 main categories and at least 30 specific types, of which Duchenne muscular dystrophy is the most common. Further types include Becker muscular dystrophy, facioscapulohumeral muscular dystrophy and myotonic dystrophy. Muscular dystrophy typically arises due to mutations in genes involved in making muscle proteins, which can be inherited or spontaneous. There is currently no cure for muscular dystrophy, although individual outcome depends on the specific type of disorder.

Sarcopenia is defined as occurring at the point at which the age-related loss of muscle function and mass becomes debilitating and impacts on quality of life (Sayer, A. A. et al. (2013) Age Ageing 42: 145-150). Sarcopenia is a multi-factorial syndrome which associates with pathophysiological changes, such as impaired neuro-muscular transition, altered excitation/contraction coupling, impaired regenerative capacity linked to stem cell exhaustion, defects of mitochondrial and energy metabolism in myofibres, and marbling of skeletal muscle with fat and fibrosis (Ali, S. et al. (2014) Gerontology 60: 294-305). The aetiology of this syndrome is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566). Sarcopenia is becoming a major health concern in developed countries, where lessened physical activity with age and increased longevity are particularly prevalent. In severe cases, sarcopenia may result in a person losing their ability to live independently. In addition, sarcopenia is a predictor of wider-ranging disability in population-based studies, and has been linked to poor balance, gait speed, prevalence of falls and fractures.

Reduced physical activity is thought to increase the likelihood of sarcopenia and therefore increased exercise will likely be beneficial in combatting the condition. Indeed, resistance exercise is associated with increased synthesis of proteins in skeletal muscle. However, exercise as a treatment often suffers from poor patient compliance.

The genetics and pathophysiology of muscle atrophy are poorly understood and there is a crucial need for effective treatments to counteract it. Several studies have demonstrated the potential of induced pluripotent stem cells (iPSCs) for the treatment of muscular dystrophy (Tedesco, F. S. et al. (2012) Science Translational Medicine 4: 140ra89; Chal, J., et al. (2015) Nature Biotechnology 33: 962-969). For example, iPSCs have been successfully used to produce multinucleated muscle fibres with organised myofibrils to model the development of the muscle lineage in vitro (Chal, J., et al. (2015) Nature Biotechnology 33: 962-969). These iPSC-derived cells are able to reconstitute muscle fibres when grafted into the muscle of dystrophic mdx mice.

However, to date it has not been explored whether it is possible to differentiate iPSCs towards the muscle lineage and stop differentiation at an early stem cell stage when the cells are not yet committed to fuse into fibres. The availability of such an uncommitted cell type would tremendously advance the options for cell therapy, for example of muscular dystrophy, since it would allow for sustained engraftment into the stem cell compartment and life-long genetic correction.

Despite decades of research, no feasible method for obtaining sufficient numbers of uncommitted muscle stem cells (MuSCs), for example for therapy of degenerative muscle diseases, exists. One of the most fundamental problems associated with stem cell therapy of the muscle is that expansion of MuSCs in conventional culture induces their terminal commitment to myogenic differentiation. This in vitro loss of stemness impairs the long-term engraftment potential of MuSCs. Upon transplantation, committed cells can only inefficiently engraft into the stem cell compartment and the majority of cells will differentiate and fuse into muscle fibres close to the injection site. This leads to poor distribution of muscle fibres containing donor nuclei in the host tissue and to transient effects that disappear with turnover of muscle fibres.

Accordingly, there remains a significant need for methods of producing muscle stem cells, in particular muscle stem cells that are uncommitted and maintain their long-term engraftment potential. Access to such muscle stem cells would facilitate significantly improved treatment of muscle diseases, in particular treatment of disorders such as myopathy, muscular dystrophy and sarcopenia, as well as aiding recovery from muscle injury.

SUMMARY OF THE INVENTION

The inventors have successfully developed a protocol for the derivation of uncommitted MuSCs from pluripotent stem cells, which mimics the conditions found in the natural MuSC niche. In contrast to existing protocols for the generation of myogenic cells from induced pluripotent stem cells (iPSCs), the inventors focused on utilising environmental conditions that allow for the generation of uncommitted cells that maintain the expression of stem cell markers (e.g. Pax7), but remain negative for commitment markers (e.g. Myf5).

To facilitate this, the inventors screened for aggregation conditions with different cell types, which induce mesoderm formation and subsequent specification to the myogenic lineage.

During these studies, the inventors screened a range of aggregation conditions with a spectrum of accessory cell lines to recapitulate the three dimensional organization of the MuSC niche.

As well as providing access to the production of uncommitted MuSCs, the inventors' approach is further advantageous in not requiring extensive use of chemicals or exogenous transcription factors.

In summary, the inventors found that co-culturing pluripotent stem cells, embryonic fibroblast cells and endothelial cells in a 3D cell culture enables the production of a population of muscle stem cells that are uncommitted and maintain their long-term engraftment potential.

Accordingly, in one aspect, the invention provides an in vitro method of producing a population of muscle stem cells comprising co-culturing pluripotent stem cells, embryonic fibroblast cells and endothelial cells in 3D cell culture.

In a preferred embodiment, the muscle stem cells are skeletal muscle stem cells.

In one embodiment, the muscle stem cells express Pax7, i.e. the muscle stem cells are Pax7$^+$. In one embodiment, the muscle stem cells express NCAM, i.e. the muscle stem cells are NCAM$^+$. In one embodiment, the muscle stem cells express CD82, i.e. the muscle stem cells are CD82$^+$.

In one embodiment, the muscle stem cells express Pax7 and NCAM, i.e. the muscle stem cells are Pax7$^+$/NCAM$^+$. In one embodiment, the muscle stem cells express Pax7 and CD82, i.e. the muscle stem cells are Pax7$^+$/CD82$^+$. In one embodiment, the muscle stem cells express NCAM and CD82, i.e. the muscle stem cells are NCAM$^+$/CD82$^+$.

In one embodiment, the muscle stem cells express Pax7, NCAM and CD82, i.e. the muscle stem cells are Pax7$^+$/NCAM$^+$/CD82$^+$.

In another aspect, the invention provides an in vitro method of producing a population of cells that express Pax7/NCAM, Pax7/CD82, NCAM/CD82 or Pax7/NCAM/CD82 comprising co-culturing pluripotent stem cells, embryonic fibroblast cells and endothelial cells in 3D cell culture.

In one embodiment, the muscle stem cells express low levels of Myf5 or substantially do not express Myf5. In a preferred embodiment, the muscle stem cells are Myf5$^-$.

In a preferred embodiment, the muscle stem cells are Pax7$^+$/Myf5$^-$.

In one embodiment, the muscle stem cells express low levels of Myogenin or substantially do not express Myogenin. In a preferred embodiment, the muscle stem cells are Myogenin-.

In a preferred embodiment, the muscle stem cells are Pax7$^+$/Myogenin$^-$.

In one embodiment, the muscle stem cells express low levels of MyoD or substantially do not express MyoD. In a preferred embodiment, the muscle stem cells are MyoD$^-$.

In a preferred embodiment, the muscle stem cells are Pax7$^+$/MyoD$^-$. In one embodiment, the muscle stem cells express low levels of MYH2 or substantially do not express MYH2. In a preferred embodiment, the muscle stem cells are MYH2$^-$.

In one embodiment, the muscle stem cells express the mesoderm marker T, i.e. the muscle stem cells are T$^+$. In one embodiment, the muscle stem cells express the mesoderm marker GATA4, i.e. the muscle stem cells are GATA4$^+$. In one embodiment, the muscle stem cells express FGF5, i.e. the muscle stem cells are FGF5$^+$.

In another aspect, the invention provides an in vitro method of producing a population of cells that are Pax7$^+$/Myf5$^-$ comprising co-culturing pluripotent stem cells, embryonic fibroblast cells and endothelial cells in 3D cell culture.

In one embodiment, the method comprises the steps:
 (a) admixing the pluripotent stem cells, embryonic fibroblast cells and endothelial cells; and
 (b) establishing at least one 3D spheroid comprising pluripotent stem cells, embryonic fibroblast cells and endothelial cells.

In one embodiment, the pluripotent stem cells are induced pluripotent stem cells or embryonic stem cells. Preferably, the pluripotent stem cells are induced pluripotent stem cells.

In one embodiment, the pluripotent stem cells are mammalian pluripotent stem cells. Preferably, the pluripotent stem cells are human pluripotent stem cells.

In one embodiment, the embryonic fibroblast cells are mammalian embryonic fibroblast cells. In one embodiment, the embryonic fibroblast cells are human embryonic fibroblast cells. In one embodiment, the embryonic fibroblast cells are mouse embryonic fibroblast cells.

In one embodiment, the embryonic fibroblast cells are non-mammalian embryonic fibroblast cells. In one embodiment, the embryonic fibroblast cells are fly, fish or worm embryonic fibroblast cells.

In one embodiment, the endothelial cells are mammalian endothelial cells. In one embodiment, the endothelial cells are human endothelial cells. In one embodiment, the endothelial cells are mouse endothelial cells.

In one embodiment, the pluripotent stem cells and embryonic fibroblast cells are in a ratio of about 0.3-4:1. In another embodiment, the pluripotent stem cells and embryonic fibroblast cells are in a ratio of about 0.5-4:1. In another embodiment, the pluripotent stem cells and embryonic fibroblast cells are in a ratio of about 0.5-3:1. In another embodiment, the pluripotent stem cells and embryonic fibroblast cells are in a ratio of about 1-3:1. In another embodiment, the pluripotent stem cells and embryonic fibroblast cells are in a ratio of about 1.5-2.5:1. In a preferred embodiment, the pluripotent stem cells and embryonic fibroblast cells are in a ratio of about 2:1.

In one embodiment, the pluripotent stem cells and endothelial cells are in a ratio of about 0.3-4:1. In another embodiment, the pluripotent stem cells and endothelial cells are in a ratio of about 0.5-3:1. In another embodiment, the pluripotent stem cells and endothelial cells are in a ratio of about 1-3:1. In another embodiment, the pluripotent stem cells and endothelial cells are in a ratio of about 1.5-2.5:1. In a preferred embodiment, the pluripotent stem cells and endothelial cells are in a ratio of about 2:1.

In one embodiment, the embryonic fibroblast cells and endothelial cells are in a ratio of about 1-2:1. In a preferred embodiment, the embryonic fibroblast cells and endothelial cells are in a ratio of about 1:1.

In one embodiment, the pluripotent stem cells, embryonic fibroblast cells and endothelial cells are in a ratio of about 0.3-8:1-2:1. In another embodiment, the pluripotent stem cells, embryonic fibroblast cells and endothelial cells are in a ratio of about 0.5-8:1-2:1. In another embodiment, the pluripotent stem cells, embryonic fibroblast cells and endothelial cells are in a ratio of about 0.5-6:1-2:1. In another embodiment, the pluripotent stem cells, embryonic fibroblast cells and endothelial cells are in a ratio of about 1-6:1-2:1. In another embodiment, the pluripotent stem cells, embryonic fibroblast cells and endothelial cells are in a ratio of about 1.5-5:1-2:1.

In one embodiment, the pluripotent stem cells, embryonic fibroblast cells and endothelial cells are in a ratio of about 0.3-4:1-2:1. In another embodiment, the pluripotent stem cells, embryonic fibroblast cells and endothelial cells are in a ratio of about 0.5-3:1-2:1. In another embodiment, the pluripotent stem cells, embryonic fibroblast cells and endothelial cells are in a ratio of about 1-3:1-2:1. In another embodiment, the pluripotent stem cells, embryonic fibroblast cells and endothelial cells are in a ratio of about 1.5-2.5:1-2:1. In another embodiment, the pluripotent stem cells, embryonic fibroblast cells and endothelial cells are in a ratio of about 2:1-2:1.

In one embodiment, the pluripotent stem cells, embryonic fibroblast cells and endothelial cells are in a ratio of about 0.3-4:1:1. In another embodiment, the pluripotent stem cells, embryonic fibroblast cells and endothelial cells are in a ratio of about 0.5-3:1:1. In another embodiment, the pluripotent stem cells, embryonic fibroblast cells and endothelial cells are in a ratio of about 1-3:1:1. In another embodiment, the pluripotent stem cells, embryonic fibroblast cells and endothelial cells are in a ratio of about 1.5-2.5:1:1. In a preferred embodiment, the pluripotent stem cells, embryonic fibroblast cells and endothelial cells are in a ratio of about 2:1:1.

In another embodiment, the pluripotent stem cells, embryonic fibroblast cells and endothelial cells are in a ratio of about 1:2:1.

In one embodiment, the pluripotent stem cells, embryonic fibroblast cells and endothelial cells are cultured for about 3-30, 3-25, 3-20, 3-15 or 3-10 days. In another embodiment, the pluripotent stem cells, embryonic fibroblast cells and endothelial cells are cultured for about 4-30, 4-25, 4-20, 4-15 or 4-10 days. In one embodiment, the pluripotent stem cells, embryonic fibroblast cells and endothelial cells are cultured for about 5-30, 5-25, 5-20, 5-15 or 5-10 days.

In another embodiment, the pluripotent stem cells, embryonic fibroblast cells and endothelial cells are cultured for about 3-30 days, preferably about 5-20 days.

In one embodiment, the culture further comprises fibroblasts other than embryonic fibroblasts, smooth muscle cells and/or myoblast cells.

In one embodiment, the fibroblasts other than embryonic fibroblasts are skeletal fibroblasts. In one embodiment, the skeletal fibroblasts are mouse or human skeletal fibroblasts, preferably mouse skeletal fibroblasts. The mouse skeletal fibroblasts may be, for example, NOR-10 cells (e.g. cells available from ATCC under the deposition number CCL-197).

In one embodiment, the fibroblasts other than embryonic fibroblasts are mouse or human fibroblasts other than embryonic fibroblasts. In one embodiment, the fibroblasts other than embryonic fibroblasts are 3T3 mouse fibroblasts. The 3T3 mouse fibroblasts may be, for example, cells available from ATCC under the deposition number CRL-1658.

In one embodiment, the smooth muscle cells are mouse or human smooth muscle cells, preferably mouse smooth muscle cells. The mouse smooth muscle cells may be, for example, MOVAS cells (e.g. cells available from ATCC under the deposition number CRL-2797).

In one embodiment, the myoblast cells are mouse or human myoblast cells, preferably mouse myoblast cells. The myoblast cells may be, for example, C2C12 mouse myoblast cells (e.g. cells available from ATCC under the deposition number CRL-1772).

In one embodiment, the cells co-cultured with the pluripotent stem cells (i.e. the embryonic fibroblast cells, endothelial cells, fibroblasts other than embryonic fibroblasts, smooth muscle cells and/or myoblast cells) are from an immortalised cell line.

In another aspect, the invention provides an isolated muscle stem cell obtainable using the method of the invention.

In another aspect, the invention provides an isolated Pax7$^+$/Myf5$^-$ muscle stem cell.

In one embodiment, the muscle stem cell is also NCAM$^+$. In another embodiment, the muscle stem cell is also CD82$^+$.

In another aspect, the invention provides the muscle stem cell of the invention for use in therapy.

In another aspect, the invention provides the muscle stem cell of the invention for use in the treatment or prevention of a muscle disease. In another aspect, the invention provides the muscle stem cell of the invention for use in the treatment or prevention of muscle atrophy. In another aspect, the invention provides the muscle stem cell of the invention for use in the treatment or prevention of myopathy. In another aspect, the invention provides the muscle stem cell of the invention for use in the treatment or prevention of muscular dystrophy. In another aspect, the invention provides the muscle stem cell of the invention for use in the treatment or prevention of sarcopenia. In a further aspect, the invention provides the muscle stem cell of the invention for use in the treatment or prevention of cachexia.

In another aspect, the invention provides the muscle stem cell of the invention for use in the treatment of muscle injury, in particular muscle injury incurred through a surgical intervention and/or trauma.

In another aspect, the invention provides a method of screening for an agent capable of increasing muscle stem cell self-renewal, proliferation or differentiation comprising the steps:
 (a) providing a population of muscle stem cells obtainable using the method of the invention;
 (b) contacting the population of muscle stem cells of step (a) with a candidate agent; and
 (c) determining whether the candidate agent increases muscle stem cell self-renewal, proliferation or differentiation.

In another aspect, the invention provides a method of screening for an agent capable of increasing muscle stem cell self-renewal, proliferation or differentiation comprising the steps:
 (a) providing a population of muscle stem cells using the method of the invention;
 (b) contacting the population of muscle stem cells of step (a) with a candidate agent; and
 (c) determining whether the candidate agent increases muscle stem cell self-renewal, proliferation or differentiation.

In another aspect, the invention provides a method of treating or preventing a muscle disease comprising administering the muscle stem cell of the invention to a subject in need of the same. In another aspect, the invention provides a method of treating or preventing muscle atrophy comprising administering the muscle stem cell of the invention to a subject in need of the same. In another aspect, the invention provides a method of treating or preventing myopathy comprising administering the muscle stem cell of the invention to a subject in need of the same. In another aspect, the invention provides a method of treating or preventing muscular dystrophy comprising administering the muscle stem cell of the invention to a subject in need of the same. In another aspect, the invention provides a method of treating or preventing sarcopenia comprising administering the muscle stem cell of the invention to a subject in need of the same. In another aspect, the invention provides a method of treating or preventing cachexia comprising administering the muscle stem cell of the invention to a subject in need of the same. In another aspect, the invention provides a method of treating muscle injury, in particular muscle injury incurred through a surgical intervention and/or trauma, comprising administering the muscle stem cell of the invention to a subject in need of the same.

In another aspect, the invention provides the use of the muscle stem cell of the invention for the manufacture of a medicament. In another aspect, the invention provides the use of the muscle stem cell of the invention for the manufacture of a medicament for the treatment or prevention of a muscle disease. In another aspect, the invention provides the use of the muscle stem cell of the invention for the manufacture of a medicament for the treatment or prevention of muscle atrophy. In another aspect, the invention provides the use of the muscle stem cell of the invention for the manufacture of a medicament for the treatment or prevention of myopathy. In another aspect, the invention provides the use of the muscle stem cell of the invention for the manufacture of a medicament for the treatment or prevention of muscular dystrophy. In another aspect, the invention provides the use of the muscle stem cell of the invention for the manufacture of a medicament for the treatment or prevention of sarcopenia. In another aspect, the invention provides the use of the muscle stem cell of the invention for the manufacture of a medicament for the treatment or prevention of cachexia. In another aspect, the invention provides the use of the muscle stem cell of the invention for the manufacture of a medicament for the treatment of muscle injury, in particular muscle injury incurred through a surgical intervention and/or trauma.

Schematic Overview of Myogenic Lineage Progression

Figure 1:
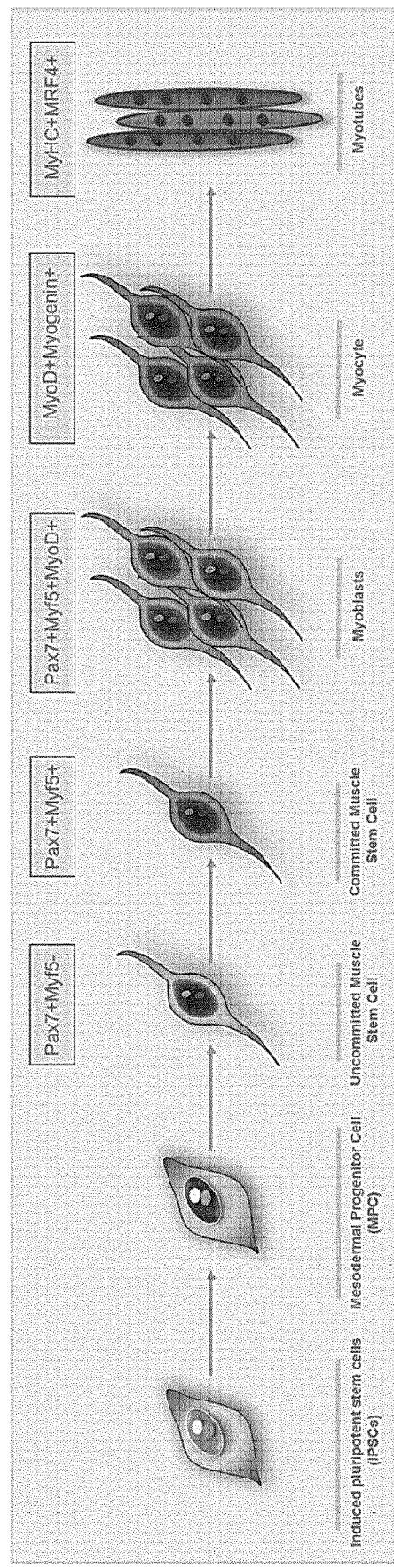
FIG. 1

Pluripotent stem cells initially enter the mesodermal lineage, progress further to a dermomyotomal fate characterized by Pax7 expression. Subsequently, cells upregulate Myf5 and are irreversibly committed to differentiation towards terminally committed post mitotic muscle fibers.

FIG. 2

IPSCs in Aggregates are Able to Undergo "BIO-FGF" Directed Muscle Lineage Differentiation A: Drugs inducing mesodermal differentiation and muscle lineage determination where applied with non-linear timing (4). Images show representative phase-contrast images of progressive changes in cell morphology. B: Pax7 expression in IPSC aggregates treated with or without different concentrations of BIO for 7 days and with FGF2 from days 7-13. Results are expressed as percentages of day 0 (Error bars, S.D.; n=3 independent experiments; ***p≤0.05 versus day 0 and control). Y-27632: RHO/ROCK pathway inhibitor; BIO (6-bromoindirubin-3'-oxime): glycogen synthase kinase-3 (GSK-3) inhibitor

FIG. 3

Derivation of MuSC from IPSC Using 3D-Niche-Mimicking Conditions

A: Schematic overview of the 3D cellular differentiation protocol. aCells=accessory cell types.

B-H: Representative morphological features of the 3D-aCell spheroids of IPSCs. EFs=embryonic fibroblasts, NOR-10=skeletal fibroblasts, 3T3 fibroblasts, endothelial cells, MOVAS=mouse smooth muscle cells and C2C12 myoblasts. Scale bars: 200 µm.

FIG. 4 qPCR Profiling of Co-Aggregates for Pax7

Results are expressed as percentage over day 0 (Error bars, S.D.; n=3 independent experiments; *p≤0.05 versus day 0 and control; p≤0.05 versus day 0 and control; *p≤0.05 versus day 0 and control).

FIG. 5

Triple Aggregate Derivation: Triple Clusters of "IPSC-EF-Endothelial" Cells Showed Robust Differentiation Towards Mesoderm and Expression of Pax7 and Remained Negative for Commitment Markers A: The triple clusters ("IPSC-MEF-Endothelial" cells) were compared to double clusters in "3D". RNA was harvested at days 0, 7, and 13 and analyzed by qPCR for Pax7 expression. Pax7 expression was significantly elevated in the triple clusters. Results are expressed as percentage over day 0 (Error bars, S.D.; n=3 independent experiments; ***p≤0.05 versus day 0 and control).

B: Pax7 expression is significantly induced when MEF added at day 7 to the double IPSC-Endothelial clusters. Results are expressed as percentage over day 0 (Error bars, S.D.; n=3 independent experiments; *p≤0.05 versus day 0 and control; p≤0.05 versus day 0 and control; *p≤0.05 versus day 0 and control).

C: Size and morphological alteration of the 3D triple-aggregates system. It shows the representative morphological features of the 3D triple clusters of "IPSC-MEF-Endothelial" cells (2:1:1). Scale bars: 200 µm.

D-F: qPCR Profiling of triple clusters of "IPSC-MEF-Endothelial" cells (2:1:1) for committed myogenic factors.

G-I: qPCR Profiling of triple clusters of "IPSC-MEF-Endothelial" cells (2:1:1) highlights a progression through the mesodermal subtypes. Results are expressed as percentage over day 0 (Error bars, S.D.; n=3 independent experiments; *p≤0.05 versus day 0 and control; p≤0.05 versus day 0 and control; *p≤0.05 versus day 0 and control).

FIG. 6

Anatomy of Aggregates with Triple Clusters of "IPSC-EF-Endothelial"

Immunohistochemistry of spheroid sections for the MuSC marker Pax7, the human differentiation marker lamin A (A-B), the endoderm marker CDX2 and the ECM protein Laminin (C). Scale bars: 50 µm.

FIG. 7

2D (Two-Dimensional) Vs 3D (Three-Dimensional) Differentiation qPCR Profiling of 2D co-culture and 3D-aggregate systems for Pax7 expression. Results are expressed as percentage over day 0 (Error bars, S.D.; n=3 independent experiments; *p≤0.05 versus day 0 and control; p≤0.05 versus day 0 and control; *p≤0.05 versus day 0 and control).

DETAILED DESCRIPTION OF THE INVENTION

The terms "comprising", "comprises" and "comprised of" as used herein are synonymous with "including" or "includes"; or "containing" or "contains", and are inclusive or open-ended and do not exclude additional, non-recited members, elements or steps. The terms "comprising", "comprises" and "comprised of" also include the term "consisting of".

Stem Cells

The muscle stem cells of the invention may be produced in vitro from pluripotent stem cells.

Stem cells are cells that have the capacity to differentiate into more specialised cells and can also divide to produce more stem cells.

Pluripotent stem cells are stem cells that may propagate indefinitely and differentiate into all cell types of the human body. These stem cells hold promise in providing a single source of cells that may replace cells affected by damage or disease.

Pluripotent stem cells may be created through a number of techniques, such as the generation of induced pluripotent stem cells or embryonic stem cells.

Preferably, the stem cells of the invention are induced pluripotent stem cells (iPSCs).

iPSCs are a type of pluripotent stem cell that may be created directly from adult cells. The skilled person is readily able to prepare iPSCs, for example by introducing specific transcription factors into adult cells or contacting adult cells with specific protein combinations.

iPSCs are advantageous over embryonic stem cells in that they overcome the need for using embryonic material and can be prepared from a subject to which they (or cells produced from them) are later re-introduced. Such autologous cell transplantation may overcome the risk of immune rejection of transplanted material.

The stem cells of the invention may be embryonic stem cells, in particular those produced without destruction of an embryo.

Methods are known in the art for producing pluripotent stem cells, such as mammalian embryonic stem cells, without the destruction of an embryo. In particular, it has been shown that mouse and human embryonic stem cells may be produced from single blastomeres while leaving the embryo intact. For example Chung, Y. et al. (2006) Nature 439: 216-219 describes methods for making mouse embryonic stem cells from a single blastomere. Later advances on this procedure provided methods where co-culturing the blastomere cell lines with other ESCs is not required (Chung, Y. et al. (2008) Cell Stem Cell 2: 113-117).

Preferably the stem cell of the invention is a mammalian stem cell, preferably a human stem cell.

Muscle Stem Cells

The term "muscle stem cell", as used herein, may refer to satellite cells, preferably satellite cells that are quiescent and are uncommitted.

Satellite cells are precursors to skeletal muscle cells. In adult muscle, satellite cells are generally quiescent, but can activate and undergo myogenesis in response to disease or mechanical strain such as injury or exercise. Satellite cells are also involved in the normal growth of muscle. Upon activation, satellite cells can proliferate. Additionally, some of these satellite cells can differentiate into myoblasts, which can fuse to form myotubes and other skeletal muscle components. The myoblasts can also augment existing muscle fibres by fusing with existing myotubes.

The methods of the invention provide for the in vitro production of muscle stem cells from pluripotent stem cells.

The muscle stem cells produced by the methods of the invention may be characterised by the expression of certain markers.

Preferably, the muscle stem cells of the invention express Pax7, i.e. preferably the muscle stem cells are Pax7$^+$. The muscle stem cells may also express NCAM and/or CD82, i.e. the muscle stem cells may be NCAM$^+$ and/or CD82$^+$.

Myf5 is a commitment marker that may be used to distinguish quiescent from committed satellite cells (FIG. 1). Preferably, the muscle stem cells of the invention express low levels of Myf5 or substantially do not express Myf5. In a preferred embodiment, the muscle stem cells are Myf5$^-$.

In a preferred embodiment, the muscle stem cells are Pax7$^+$/Myf5$^-$.

MYH2 is another commitment marker. Preferably, the muscle stem cells of the invention express low levels of MYH2 or substantially do not express MYH2. In a preferred embodiment, the muscle stem cells are MYH2$^-$.

Further markers may also be used to characterise the muscle stem cells of the invention, for example the mesoderm markers T and GATA4, and FGF5. In one embodiment, the muscle stem cells express the mesoderm marker T, i.e. the muscle stem cells are T$^+$. In one embodiment, the muscle stem cells express the mesoderm marker GATA4, i.e. the muscle stem cells are GATA4$^+$. In one embodiment, the muscle stem cells express FGF5, i.e. the muscle stem cells are FGF5$^+$.

Analysis of marker expression may be readily carried out by the skilled person using any suitable technique, for example flow cytometry or quantitative PCR (qPCR).

Muscle stem cells can also be identified by their morphology. For example, muscle stem cells may have a high nuclear-to-cytoplasmic volume ratio in comparison to myoblast, fibroblast or epithelial cells. They may also have fewer organelles compared to myoblast, fibroblast or epithelial cells. Muscle stem cells may have a large quantity of nuclear heterochromatin relative to myonuclei. Activated muscle stem cells may have an increased number of caveolae, cytoplasmic organelles and decreased levels of heterochromatin compared to quiescent muscle stem cells. Furthermore, muscle stem cells may be less elongated and less spindle-shaped compared to myoblasts.

Preferably, the muscle stem cells are capable of forming myoblasts, particularly myoblasts that can fuse to form myotubes. This capability can be detected functionally, such as by demonstrating differentiation into myoblasts or myotubes, which can be carried out in vitro or in vivo.

Muscle Diseases, Disorders and Injury

Muscle diseases and disorders, both developmental and degenerative, can cause the gradual or sudden loss of muscle function due to the decline or death of muscle cells, as well as lessened muscular development due to developmental diseases. Congenital myopathies are examples of muscular diseases that present these characteristics. Muscle loss may also occur from aging, from the treatment of diseases or from a number of other causes. Examples of these types of muscle loss include sarcopenia and cachexia.

Muscle Function, Mass and Atrophy

The muscle stem cells and uses thereof disclosed herein may be used to provide for the maintenance of or increase in muscle function and/or mass.

The term "muscle function", as used herein, may refer to the ability of a muscle to perform in a manner that does not negatively impact on the life of a subject, and encompasses parameters of muscle strength, muscle contraction, muscle endurance and/or muscle elasticity.

Suitable tests for assessing muscle function include grip strength assessment using a dynamometer; one repeat maximum on leg press, chest press or leg extension; gait speed; 6 min walk test; time up and go; short physical performance battery; Fried frailty criteria; and stair climbing time assessments.

Muscle mass (which may equate with muscle volume, muscle thickness or myofibre size) may be measured by dual-energy X-ray absorptiometry (DXA) or bioimpedance tests. Similarly, MRI may be used for assessing muscle volume and ultra-sound may be used for assessing muscle thickness and pennation angle.

The terms "muscle atrophy" and "muscle wasting", as used herein, may refer to a reduction in muscle mass, for example to the stage where the muscle loss becomes debilitating. In one embodiment, the subject to whom the muscle stem cells of the invention are administered does not lose more than 10%, 5%, 4%, 3%, 2% or 1% of their muscle mass.

Preferably, the muscle stem cells and uses thereof disclosed herein provide for the maintenance of or increase in muscle mass.

The term "maintains", as used herein, refers to a particular parameter, such as muscle function and/or mass, remaining substantially unchanged over a period of time (e.g. 5, 10, 15, 20, 25, 30, 40, 50 or more years).

In one embodiment, muscle mass increases (in the subject to whom the muscle stem cells of the invention are administered) by at least 1%, 2%, 3%, 4%, 5%, 10%, 15% or 20%.

In another embodiment, muscle mass increases (in the subject to whom the muscle stem cells of the invention are administered) by 1-2.5%, 1-5%, 1-10% or 1-20%.

Preferably, the muscle is skeletal muscle.

Myopathy

The muscle stem cells and uses thereof disclosed herein may be used to treat or prevent myopathy.

Myopathies are neuromuscular disorders in which the main symptom is muscle weakness due to dysfunction of muscle fibres. Further symptoms include, for example, muscle cramp, stiffness and spasm.

Myopathies can be inherited (e.g. muscular dystrophies) or acquired (e.g. muscle cramps), and may be classified into a number of groups: congenital myopathies are characterised by developmental delays in motor skills, and skeletal and facial abnormalities may be evident at birth; muscular dystrophies are characterised by progressive weakness in voluntary muscles; mitochondrial myopathies are caused by genetic abnormalities in mitochondria; muscle glycogen storage diseases, including Pompe's, Andersen's and Cori's diseases; myoglobinurias are caused by disorders in myoglobin metabolism; dermatomyositis; myositis ossificans, which is characterised by bone growth in muscle; familial periodic paralysis; polymyositis and inclusion body myositis; neuromyotonia; stiff-man syndrome; common muscle cramps and stiffness; and tetany.

Muscular Dystrophy

The muscle stem cells and uses thereof disclosed herein may be used to treat or prevent muscular dystrophy.

Muscular dystrophy is a group of disorders that result in the weakening and breakdown of skeletal muscles. This group comprises 9 main categories and at least 30 specific types, of which Duchenne muscular dystrophy is the most common. Further types include Becker muscular dystrophy, facioscapulohumeral muscular dystrophy and myotonic dystrophy.

Muscular dystrophy typically arises due to mutations in genes involved in making muscle proteins, which can be inherited.

Cachexia

The invention provides a method of addressing cachexia or wasting syndrome. Cachexia is a complex metabolic syndrome associated with underlying illness and characterized by loss of muscle with or without loss of fat mass. The prominent clinical feature of cachexia is weight loss in adults (corrected for fluid retention) or growth failure in children (excluding endocrine disorders). Cachexia is often seen in patients with diseases such as cancer, AIDS, coeliac disease, chronic obstructive pulmonary disease, chronic heart failure, chronic kidney disease, chronic pancreatitis and/or metabolic acidosis.

Sarcopenia

The invention provides a means to address muscle atrophy. Age-related loss of muscle function and mass occurs inevitably in all individuals, however its progression depends on a range of genetic and environmental factors, such as physical activity and nutritional intake.

The specific condition of sarcopenia is defined as occurring at the point at which the age-related loss of muscle mass and function becomes debilitating and impacts on quality of life (Sayer, A. A. et al. (2013) Age Ageing 42: 145-150).

Sarcopenia is a multi-factorial syndrome that associates with pathophysiological changes, such as impaired neuromuscular transition, altered excitation/contraction coupling, impaired regenerative capacity linked to stem cell exhaustion, defects of mitochondrial and energy metabolism in myofibres, and marbling of skeletal muscle with fat and fibrosis (Ali, S. et al. (2014) Gerontology 60: 294-305). The aetiology of these syndromes is therefore complex and poorly understood, but low physical activity, hormonal decline in anabolic hormones (e.g. androgens and IGF-1), and malnutrition and/or nutritional deficiencies play an important role (Mithal, A. et al. (2013) Osteoporos. Int. 24: 1555-1566).

Muscle Injury

Acute muscle degeneration is characterised by a strong destruction of the muscle fibres, and an infiltration of immune cells into the muscle. The role of the immune response during muscle regeneration is critical and has to be properly coordinated. Neutrophils and pro-inflammatory macrophages first invade the muscle and participate in the clearance of muscle debris post-injury. The immune cell population then switches to anti-inflammatory macrophages which sustain muscle regeneration. The sequential secretion of cytokines by immune cells is thus finely orchestrated during the first few days after muscle injury and modulates the activity of the muscle progenitors. Indeed, numerous muscle-resident progenitor cells start to activate and proliferate once the muscle debris has been cleared, and will soon engage into specific lineage commitment to regenerate the muscle. In particular, the muscle stem cells (satellite cells, SATs) proliferate and eventually differentiate into muscle fibres. Mesenchymal non-myogenic progenitor cells, or fibro/adipogenic progenitors (FAPs) are also activated at the same time in order to sustain myogenesis. 7 days after muscle injury, most progenitor populations have committed, and the immune response has been resolved. By 14 days after injury, the muscle is composed of newly formed myofibres and most signals have returned to basal level.

The muscle stem cells and uses thereof disclosed herein may be used for treating, preventing or reducing the detrimental effects of muscle injury.

In one embodiment, the subject has incurred muscle injury through a surgical intervention and/or trauma.

The term "surgical intervention", as used herein, may refer to any surgical approach that results in damage to muscle. Thus, the muscle stem cells and uses thereof disclosed herein may be used in aiding recovery after a surgical procedure.

The term "trauma", as used herein, may refer to an unplanned event that results in injury of a muscle, for example an accident or sporting injury.

In another embodiment, the subject is to undergo a planned surgical intervention. For example, the muscle stem cells and uses thereof disclosed herein may be applied to a subject who is scheduled to undergo surgery in less than 1 month, or less than 3, 2 or 1 weeks.

Method of Treatment

All references herein to treatment include curative, palliative and prophylactic treatment; although in the context of the invention references to prevention are more commonly associated with prophylactic treatment. Treatment may also include arresting progression in the severity of a disease. The treatment of mammals, particularly humans, is preferred. Both human and veterinary treatments are within the scope of the invention.

Administration

Although the muscle stem cells for use in the invention can be administered alone, they will generally be administered in admixture with a pharmaceutical carrier, excipient or diluent, particularly for human therapy. Suitable carriers and diluents include isotonic saline solutions, for example phosphate-buffered saline, and potentially contain human serum albumin.

Transplantation

The muscle stem cells of the invention may be, for example, administered to a subject as part of an autologous cell transplant procedure or as part of an allogeneic cell transplant procedure.

The term "autologous cell transplant procedure" refers to a procedure in which the precursor cells (from which the muscle stem cells of the invention are produced) are obtained from the same subject as that to which the muscle stem cells of the invention are administered.

Autologous transplant procedures are advantageous as they avoid problems associated with immunological incompatibility and are accessible to subjects irrespective of the availability of a genetically matched donor.

Cells transplanted in an autologous cell transplant procedure may have been genetically modified (e.g. using gene therapy approaches) to introduce correctly functioning genes and/or delete dysfunctional genes. Such an approach may find particular use in the treatment of inherited disorders, such as muscular dystrophy.

The term "allogeneic cell transplant procedure" refers to a procedure in which the precursor cells (from which the muscle stem cells of the invention are produced) are obtained from a different subject as that to which the muscle stem cells of the invention are administered.

Preferably, the donor will be genetically matched to the subject to which the muscle stem cells are administered to minimise the risk of immunological incompatibility.

Dosage

The skilled person can readily determine an appropriate dose of an agent of the invention to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can of course be individual instances where higher or lower dosage ranges are merited, and such are within the scope of the invention.

Subject

The term "subject", as used herein, may refer to either a human or non-human animal.

Examples of non-human animals include vertebrates, for example mammals, such as non-human primates (particularly higher primates), dogs, rodents (e.g. mice, rats or guinea pigs), pigs and cats. The non-human animal may be a companion animal.

Preferably, the subject is a human.

Methods of Production

In one aspect, the invention provides an in vitro method of producing a population of muscle stem cells comprising co-culturing pluripotent stem cells, embryonic fibroblast cells and endothelial cells in three-dimensional (3D) cell culture.

In one embodiment, the method comprises the steps:
(a) admixing the pluripotent stem cells, embryonic fibroblast cells and endothelial cells; and
(b) establishing at least one 3D spheroid comprising pluripotent stem cells, embryonic fibroblast cells and endothelial cells.

3D cell culture is an artificially-created environment which enables cells to grow or interact with their surroundings in three dimensions. In such culture, cells typically form 3D colonies, which may be referred to as "spheroids". The 3D culture approach may more accurately model the cells' in vivo growth and behaviour.

The skilled person is readily able to carry out 3D cell culture, for example by taking advantage of any of a number of commercially-available culturing tools. For example, the 3D culture may be carried out using scaffold or scaffold-free techniques.

Scaffold-based techniques make use of supports such as solid scaffolds and hydrogels to enable the cells to form a 3D culture. Such scaffolds may aim to mimic the natural extracellular matrix (ECM), which is present in vivo.

Scaffold-free techniques dispense with the use of the scaffold on which to grow the cells. Instead, 3D spheroids may be established through the use of, for example, low-adhesion plates, hanging-drop plates, micro-patterned surfaces, rotating bioreactors, magnetic levitation and magnetic 3D bioprinting.

Establishment of the pluripotent stem cell, embryonic fibroblast cell and endothelial cell co-aggregate 3D spheroid may be achieved, for example, by culturing in ultra-low attachment plates and/or using a shaker platform at about 80-120 RPM or 90-110 RPM, preferably about 100 RPM. Establishment of the initial co-aggregate may be achieved following incubation, for example, for about 6-18 h or 9-15 h, preferably about 12 h.

Following establishment of the at least one 3D spheroid comprising pluripotent stem cells, embryonic fibroblast cells and endothelial cells, the co-culture of step (b) may be incubated for a suitable period of time to produce the desired population of cells. Thus, in one embodiment the method may further comprise the step:
(c) incubating the co-culture of step (b) under conditions suitable for the production of the muscle stem cells.

The cell cultures during the methods of the invention may be carried out using any suitable cell culture medium. In one embodiment, the cell culture medium is APEL medium.

APEL medium is a serum-free and animal component-free medium specifically developed to support human pluripotent stem cell differentiation. An example composition of APEL medium is:
Iscove's modified Dulbecco's medium (IMDM)/Ham's F-12 nutrient mixture (1:1), supplemented with recombinant human albumin (5 mg/mL), deionised BSA (2.5 mg/mL), polyvinylalcohol (PVA), linoleic acid (100 ng/mL), synthetic cholesterol (2.2 µg/mL), α-monothioglycerol (α-MTG, 350-450 μM), recombinant human Insulin-transferrin-selenium-ethanolamine solution (rhITS-Eth, X1), protein-free hybridoma mixture II (PFHMII, 5%), ascorbic acid 2-phosphate (50 μg/mL), L-alanyl-L-glutamine (2 mM) and penicillin/streptomycin mix solution.

Preferably, the cell culture medium comprises a ROCK inhibitor, for example Y-27632. The ROCK inhibitor may be included at a concentration of, for example, about 5-15, 6-14, 7-13, 8-12 or 9-11 μM, preferably about 10 μM.

The co-culture of pluripotent stem cells, embryonic fibroblast cells and endothelial cells may be carried out for any suitable period of time. The duration of culture may be controlled by monitoring the expression of relevant muscle stem cell markers (e.g. Pax7, NCAM, CD82, Myf5, MYH2, T, GATA4 and/or FGF5; preferably at least Pax7 and/or Myf5), and culture may be stopped when expression of the muscle stem cell marker achieves a reference level and/or begins to change from a reference level.

In one embodiment, the pluripotent stem cells, embryonic fibroblast cells and endothelial cells are cultured for about 3-30, 3-25, 3-20, 3-15 or 3-10 days. In another embodiment, the pluripotent stem cells, embryonic fibroblast cells and endothelial cells are cultured for about 4-30, 4-25, 4-20, 4-15 or 4-10 days. In one embodiment, the pluripotent stem cells, embryonic fibroblast cells and endothelial cells are cultured for about 5-30, 5-25, 5-20, 5-15 or 5-10 days.

In another embodiment, the pluripotent stem cells, embryonic fibroblast cells and endothelial cells are cultured for about 3-30 days, preferably about 5-20 days.

Suitable culture conditions for use in the methods of the invention include, for example:
(a) culturing at about 36-38° C. or 36.5-37.5° C., preferably about 37° C.;
(b) culturing at about 4-6% or 4.5-5.5% $CO_2$, preferably about 5% $CO_2$; and/or
(c) culturing at least about 95%, 96%, 97%, 98% or 99% humidity, preferably about 100% humidity.

Any suitable number of pluripotent stem cells may be added at the start of the methods of the invention. For example, about 1-10 million, 2-9 million, 3-8 million, 4-7 million or 5-6 million pluripotent stem cells may be added at the start of the methods of the invention.

The additional cells to be co-cultured with the pluripotent stem cells (i.e. the embryonic fibroblast cells, endothelial cells, fibroblasts other than embryonic fibroblasts, smooth muscle cells and/or myoblast cells) may be added to the pluripotent stem cells to establish any suitable ratio.

In one embodiment, the pluripotent stem cells and embryonic fibroblast cells are in a ratio of about 0.3-4:1. In another embodiment, the pluripotent stem cells and embryonic fibroblast cells are in a ratio of about 0.5-4:1. In another embodiment, the pluripotent stem cells and embryonic fibroblast cells are in a ratio of about 0.5-3:1. In another embodiment, the pluripotent stem cells and embryonic fibroblast cells are in a ratio of about 1-3:1. In another embodiment, the pluripotent stem cells and embryonic fibroblast cells are in a ratio of about 1.5-2.5:1. In a preferred embodiment, the pluripotent stem cells and embryonic fibroblast cells are in a ratio of about 2:1.

In one embodiment, the pluripotent stem cells and endothelial cells are in a ratio of about 0.3-4:1. In another embodiment, the pluripotent stem cells and endothelial cells are in a ratio of about 0.5-3:1. In another embodiment, the pluripotent stem cells and endothelial cells are in a ratio of about 1-3:1. In another embodiment, the pluripotent stem cells and endothelial cells are in a ratio of about 1.5-2.5:1.

In a preferred embodiment, the pluripotent stem cells and endothelial cells are in a ratio of about 2:1.

In one embodiment, the embryonic fibroblast cells and endothelial cells are in a ratio of about 1-2:1. In a preferred embodiment, the embryonic fibroblast cells and endothelial cells are in a ratio of about 1:1.

In one embodiment, the pluripotent stem cells, embryonic fibroblast cells and endothelial cells are in a ratio of about 0.3-8:1-2:1. In another embodiment, the pluripotent stem cells, embryonic fibroblast cells and endothelial cells are in a ratio of about 0.5-8:1-2:1. In another embodiment, the pluripotent stem cells, embryonic fibroblast cells and endothelial cells are in a ratio of about 0.5-6:1-2:1. In another embodiment, the pluripotent stem cells, embryonic fibroblast cells and endothelial cells are in a ratio of about 1-6:1-2:1. In another embodiment, the pluripotent stem cells, embryonic fibroblast cells and endothelial cells are in a ratio of about 1.5-5:1-2:1.

In one embodiment, the pluripotent stem cells, embryonic fibroblast cells and endothelial cells are in a ratio of about 0.3-4:1-2:1. In another embodiment, the pluripotent stem cells, embryonic fibroblast cells and endothelial cells are in a ratio of about 0.5-3:1-2:1. In another embodiment, the pluripotent stem cells, embryonic fibroblast cells and endothelial cells are in a ratio of about 1-3:1-2:1. In another embodiment, the pluripotent stem cells, embryonic fibroblast cells and endothelial cells are in a ratio of about 1.5-2.5:1-2:1. In another embodiment, the pluripotent stem cells, embryonic fibroblast cells and endothelial cells are in a ratio of about 2:1-2:1.

In one embodiment, the pluripotent stem cells, embryonic fibroblast cells and endothelial cells are in a ratio of about 0.3-4:1:1. In another embodiment, the pluripotent stem cells, embryonic fibroblast cells and endothelial cells are in a ratio of about 0.5-3:1:1. In another embodiment, the pluripotent stem cells, embryonic fibroblast cells and endothelial cells are in a ratio of about 1-3:1:1. In another embodiment, the pluripotent stem cells, embryonic fibroblast cells and endothelial cells are in a ratio of about 1.5-2.5:1:1. In a preferred embodiment, the pluripotent stem cells, embryonic fibroblast cells and endothelial cells are in a ratio of about 2:1:1.

In another embodiment, the pluripotent stem cells, embryonic fibroblast cells and endothelial cells are in a ratio of about 1:2:1.

The ratios disclosed herein are preferably the ratios upon initial admixing of the cells.

Once the culture is complete, the 3D spheroids may be dissociated to a population of single cells and may then be passed through a flow cytometer (e.g. for analysis). In order to digest the spheroids into single cells, enzymes with proteolytic and collagenolytic activities may be utilised, such as accutase or trypsin. A cell aggregate dissociation medium such as accumax may also be used.

The dissociated cells may then be analysed and/or sorted based on certain markers, such as Pax7, NCAM/CD56, Pax3, CD82, Myf5, MYH2, T, GATA4 and/or FGF5.

Alternatively or additionally, the 3D spheroids may be used directly for screening purposes, for example in a method of screening of the invention. Such methods may facilitate an accurate study of a range of in vivo biological processes, including muscle stem cell niche functions and muscle tissue responses to different chemicals and drugs.

Embryonic Fibroblast Cells

Embryonic fibroblast (EF) cells are often utilised as feeder cells in stem cell research. They are the most common cell present in the connective tissue in animals, and can synthesise the extracellular matrix and collagen, the structural framework for animal tissues. In addition, embryonic fibroblast cells are known to play a role in wound healing.

Mouse embryonic fibroblasts (MEF) have been used as a surrogate stem cell model for postnatal bone marrow-derived stromal stem cells in order to study mesoderm-type cell differentiation such as osteoblasts, adipocytes and also chondrocytes.

Embryonic fibroblast cells are derived from the primitive mesenchyme, like all connective tissue cells. Their ability to express vimentin indicates their mesodermal origin.

An example of a suitable embryonic fibroblast cell is MEF (CF-1) available from ATCC under the deposition number SCRC-1040.

Endothelial Cells

Endothelial cells line the inside of every blood vessel inside the body, forming a thick layer called the endothelium. The endothelium creates the blood vessel wall and is combined with thicker layers of muscle cells and elastic fibres in the larger blood vessels (e.g. veins and arteries).

The main natural function of endothelial cells is to form a barrier between the blood and other tissues. Adult endothelial cells preserve remarkable plasticity and are known to reprogram in response to IL-1, TNF, VEGF and FGF.

Endothelial cells express a number of surface markers including CD31/PECAM-1, CD34, VE-Cadherin, CD45, CD117/c-kit, CD133, CXCR4, ETV2/ER71, MCAM/CD146, Tie-2 and VEGF R2/KDR/Flk-1.

An example of a suitable endothelial cell is C166 available from ATCC under the deposition number CRL-2581.

Additional Accessory Cells

In addition to the embryonic fibroblast cells and endothelial cells, further types of cell may be included in the co-culture during production of the muscle stem cells of the invention.

In one embodiment, the culture further comprises fibroblasts other than embryonic fibroblasts, smooth muscle cells and/or myoblast cells.

In one embodiment, the fibroblasts other than embryonic fibroblasts are skeletal fibroblasts. In one embodiment, the skeletal fibroblasts are mouse or human skeletal fibroblasts, preferably mouse skeletal fibroblasts. The mouse skeletal fibroblasts may be, for example, NOR-10 cells (e.g. cells available from ATCC under the deposition number CCL-197).

In one embodiment, the fibroblasts other than embryonic fibroblasts are mouse or human fibroblasts other than embryonic fibroblasts. In one embodiment, the fibroblasts other than embryonic fibroblasts are 3T3 mouse fibroblasts. The 3T3 mouse fibroblasts may be, for example, cells available from ATCC under the deposition number CRL-1658.

In one embodiment, the smooth muscle cells are mouse or human smooth muscle cells, preferably mouse smooth muscle cells. The mouse smooth muscle cells may be, for example, MOVAS cells (e.g. cells available from ATCC under the deposition number CRL-2797).

In one embodiment, the myoblast cells are mouse or human myoblast cells, preferably mouse myoblast cells. The myoblast cells may be, for example, C2C12 mouse myoblast cells (e.g. cells available from ATCC under the deposition number CRL-1772).

Method of Screening

In another aspect, the invention provides a method of screening for an agent capable of increasing muscle stem cell self-renewal, proliferation or differentiation comprising the steps:

(a) providing a population of muscle stem cells obtainable using the method of the invention;
(b) contacting the population of muscle stem cells of step (a) with a candidate agent; and
(c) determining whether the candidate agent increases muscle stem cell self-renewal, proliferation or differentiation.

Preferably, the method is an in vitro method.

Stem cell self-renewal is the capability of a stem cell to undergo multiple cycles of cell division, while maintaining an undifferentiated state. Proliferation may refer to the expansion of cells by division of single cells into two daughter cells. Stem cells may proliferate by dividing to form one daughter cell that remains a stem cell and a second daughter cell that becomes more differentiated. Differentiation may refer to a change in type of cell, in particular a change that results in a cell becoming more specialised.

Stem cell self-renewal, proliferation and differentiation may be readily analysed by the skilled person, for example by analysing the expression of markers (e.g. in the case of muscle stem cells, markers such as Pax7, NCAM, CD82, Myf5, MYH2, T, GATA4 and/or FGF5). Suitable methods for analysing marker expression include flow cytometry and quantitative PCR (qPCR).

In one embodiment, the population of muscle stem cells are in the form of 3D spheroids. In another embodiment, the population of muscle stem cells are in the form of a population of single cells, preferably that have been dissociated from 3D spheroids.

The candidate agent may be, for example, a pharmaceutical agent or nutritional supplement. Preferably, the candidate agent is a nutritional supplement. The term "nutritional supplement", as used herein, may refer to a product which is intended to supplement the general diet of a subject.

In one embodiment, the candidate agent is comprised in a library of candidate agents.

The effect of the candidate agent may be assessed as a function of time, by carrying out repeated measurements over a particular time-course.

Determining whether the candidate agent increases muscle stem cell self-renewal, proliferation or differentiation may be carried out by comparing any effect on self-renewal, proliferation or differentiation in the presence of the candidate agent to the level of muscle stem cell self-renewal, proliferation or differentiation in its absence, for example using a control experiment or pre-determined reference level.

The skilled person will understand that they can combine all features of the invention disclosed herein without departing from the scope of the invention as disclosed.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1

In order to engineer a niche-mimicking 3D model that allows for the derivation of uncommitted muscle stem cells (MuSCs) from iPSCs, we developed a co-aggregation assay with different types of cells that would typically surround MuSCs during development or adulthood. These cell types include mouse embryonic fibroblasts (MEFs), mouse skeletal fibroblasts (NOR-10), 3T3 mouse fibroblasts, endothelial cells, mouse smooth muscle cells (MOVAS) and C2C12 mouse myoblasts.

Aggregates

Figure 2:
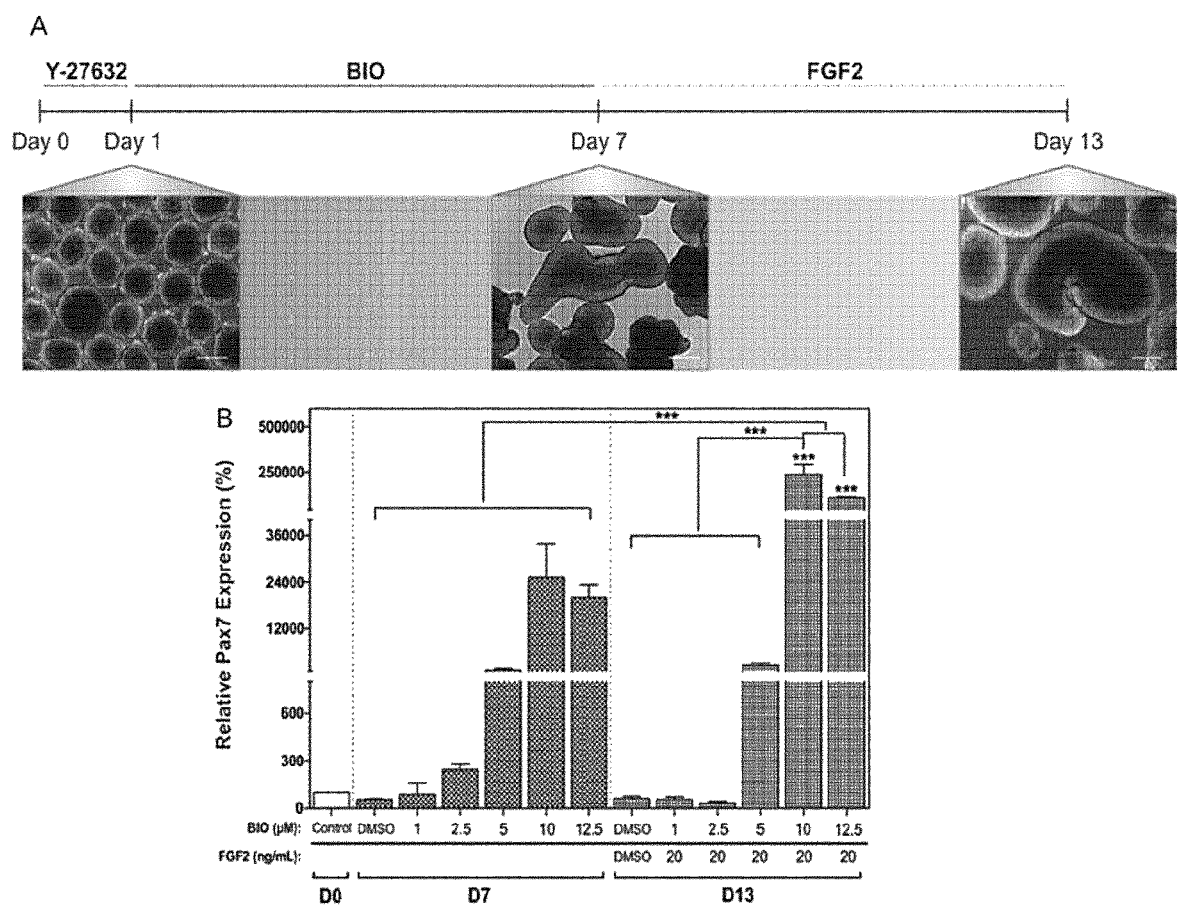

Aggregates were prepared using ultra-low attachment plates on a planar shaker platform. We first decided to test a chemical protocol for the derivation of myogenic cells that has been established in 2D culture in our 3D aggregation system (Shelton, M. et al. (2014) Stem Cell Reports 3: 516-529) as outlined in FIG. 2A. Analysis by quantitative PCR (qPCR) showed significant upregulation of PAX7 with the chemical treatment (FIG. 2B). Thus, we were able to efficiently derive myogenic cells in our 3D system using established drug-based protocols.

Figure 3:
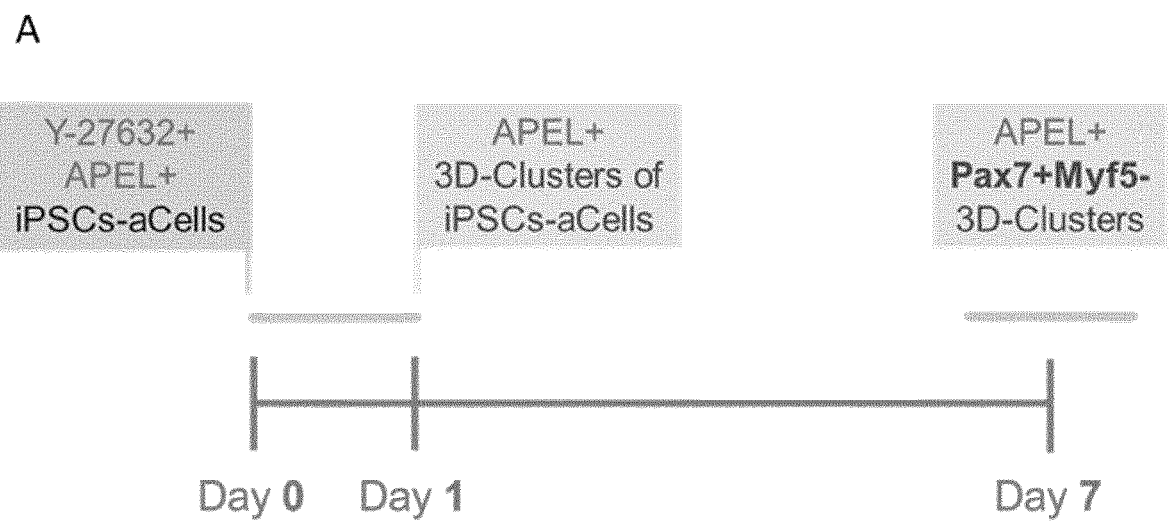
Figure 4:
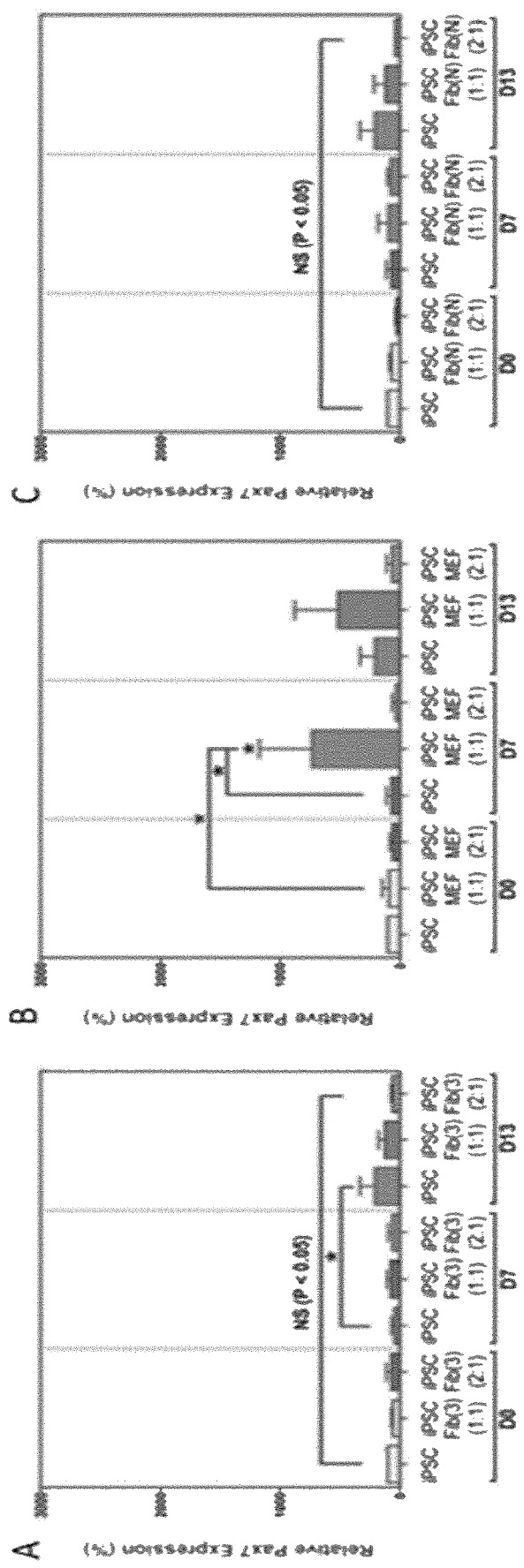

Next, we investigated the effect of co-aggregation of niche cells with the iPSCs. The schematic protocol is shown in FIG. 3A. To this end, iPSC and other cell suspensions were pre-mixed at different ratios (FIG. 3B-H). Assessment of Pax7 expression by qPCR revealed an induction at day 7 and 14 under the co-aggregation conditions (1:1) for MEF, endothelial cells and myoblasts. The type and ratio of support cells to iPSCs was also critical for Pax7 induction. MEFs, endothelial cells and mouse myoblasts were support cells that particularly promoted the differentiation of iPSCs into Pax7+ cells.

In a typical experiment, co-aggregates were prepared by pipetting 5.5 million iPS cells and niche cells in 6-well ultra-low attachment plates (Corning, Corning, N.Y.) to allow overnight spheroid aggregation on the shaker platform set at 100 RPM. For this 3D co-culture experiment, iPSC and other cell suspensions were pre-mixed at certain ratios (e.g. 1:1 and 2:1 ratios) at day 0. All cultures were maintained in a humidified incubator at 37° C., 5% $CO_2$, and 100% humidity. The aggregation APEL media (Stemcell Technologies, Vancouver, BC), which contains Y-27632 (ROCK Inhibitor) at 10 µM was used for 14 days. Then, we screened for niche-mimicking aggregation conditions inducing mesoderm formation and subsequent specification to the myogenic lineage.

Figure 5:
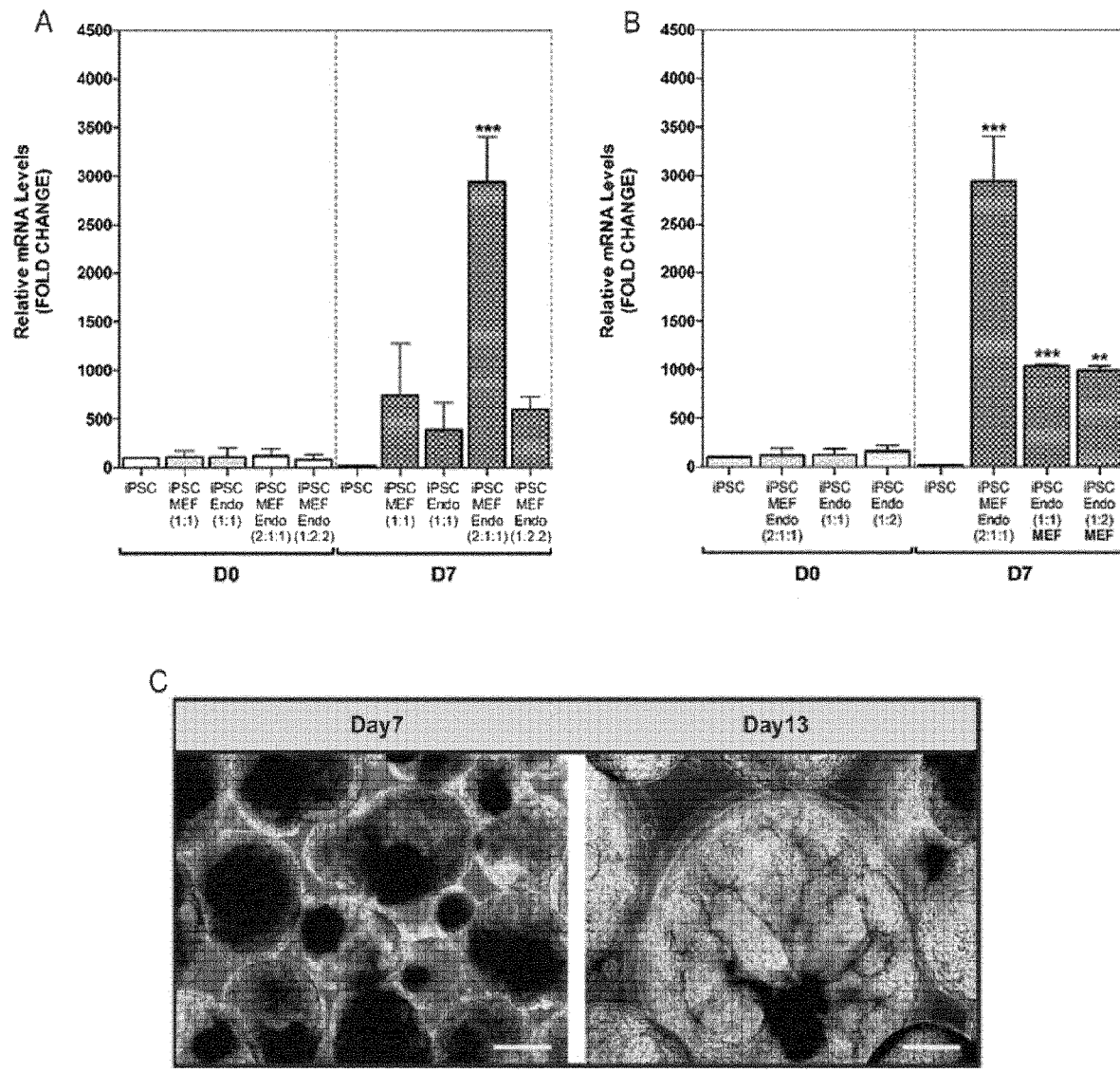

Based on the above results, we aggregated iPSCs, MEFs and endothelial cells in triple clusters (FIG. 5A). Pax7 expression was significantly elevated in the triple clusters of "iPSC-MEF-Endothelial" cells (2:1:1) at day 7 compared to the double-clusters of iPSC-MEF and iPSC-Endothelial cells (FIG. 5A). Spheroids showed a budding morphology until day 7 and were composed of a confluent layer of cells on the surface with hollow structures inside at day 14 (FIG. 5C). Moreover, tubular- or capillary-like networks became apparent inside the aggregates at day 14 (FIG. 5C).

We also prepared aggregates composed of iPSC-Endothelial cells to which MEFs were added at day 7 (FIG. 5B). Pax7 expression was significantly induced by MEFs involvement compared to the iPSC-Endothelial double clusters alone (FIG. 5B). However, co-aggregation of all 3 cell types from the beginning was more efficient.

We next analysed the expression of key myogenic genes and commitment markers by quantitative PCR (qPCR) (FIG. 5D-F). Neither Pax3, nor the commitment and differentiation markers Myf5 and MYH2 were significantly induced (FIG. 5D-F). Importantly, mesoderm markers T and GATA4 were strongly induced (FIG. 5G-H). Interestingly, we also observed a significant increase in the expression of the ectoderm marker FGF5 (FIG. 5I). In conclusion, triple clusters equipped with iPSC-MEF-Endothelial cells showed robust differentiation towards mesoderm, showed expression of Pax7 and remained negative for commitment markers.

Figure 6:
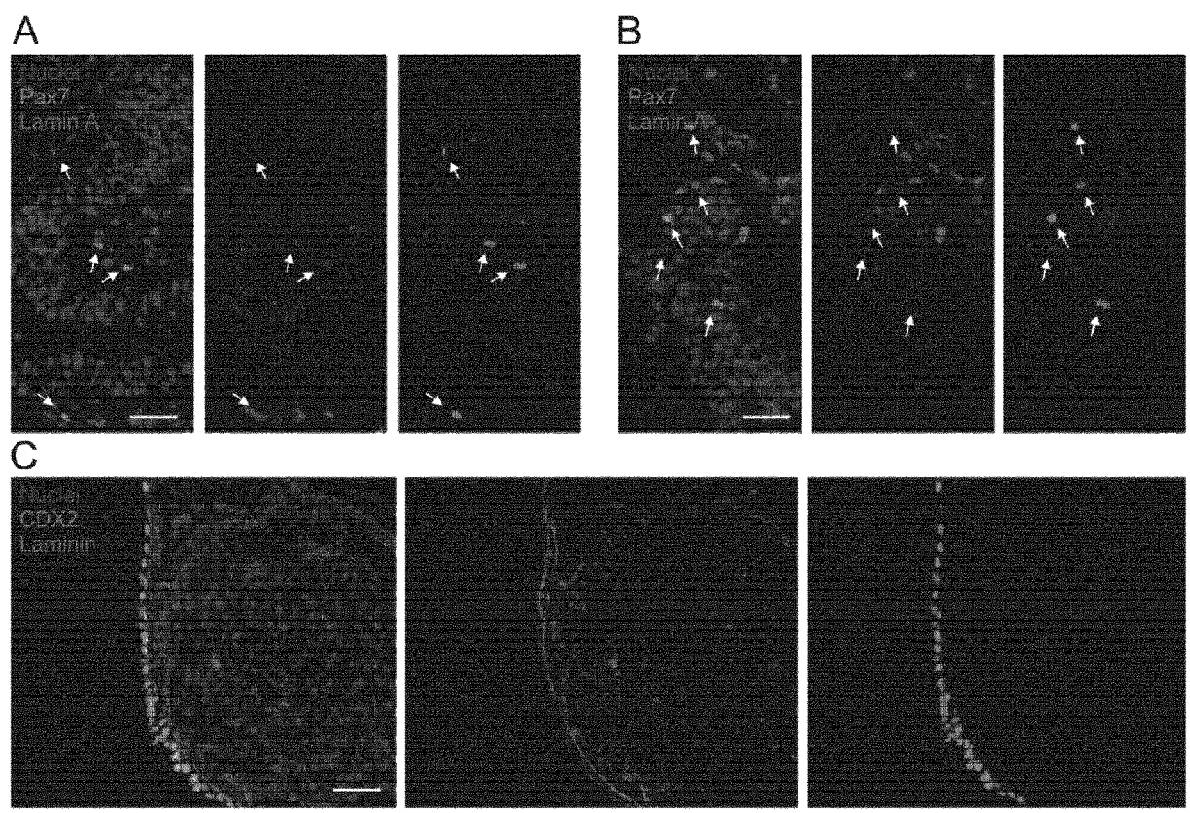

To assess the anatomy of mature aggregates at day 13 we performed immunostaining for Pax7, Lamin A, CDX2 and Laminin (FIG. 6). Cross-sections of the spheroids revealed central cells positive for Pax7 after 13 days in culture (FIG. 6A-B). Confirming their stem cell character, most of the Pax7+ processor cells are negative for the differentiation marker Lamin A (human specific) (Constantinescu, D. et al. (2006) Stem Cells 24 177-185). We also performed immunostaining for Laminin, an extra-cellular matrix (ECM) molecule, which is strongly expressed in the basement membrane of skeletal muscle tissue (FIG. 6C). Many aggregates showed a high level of self-organisation with epithelial structures that are positive for the intestinal endoderm marker CDX2 in the cluster (FIG. 6C).

Figure 7:
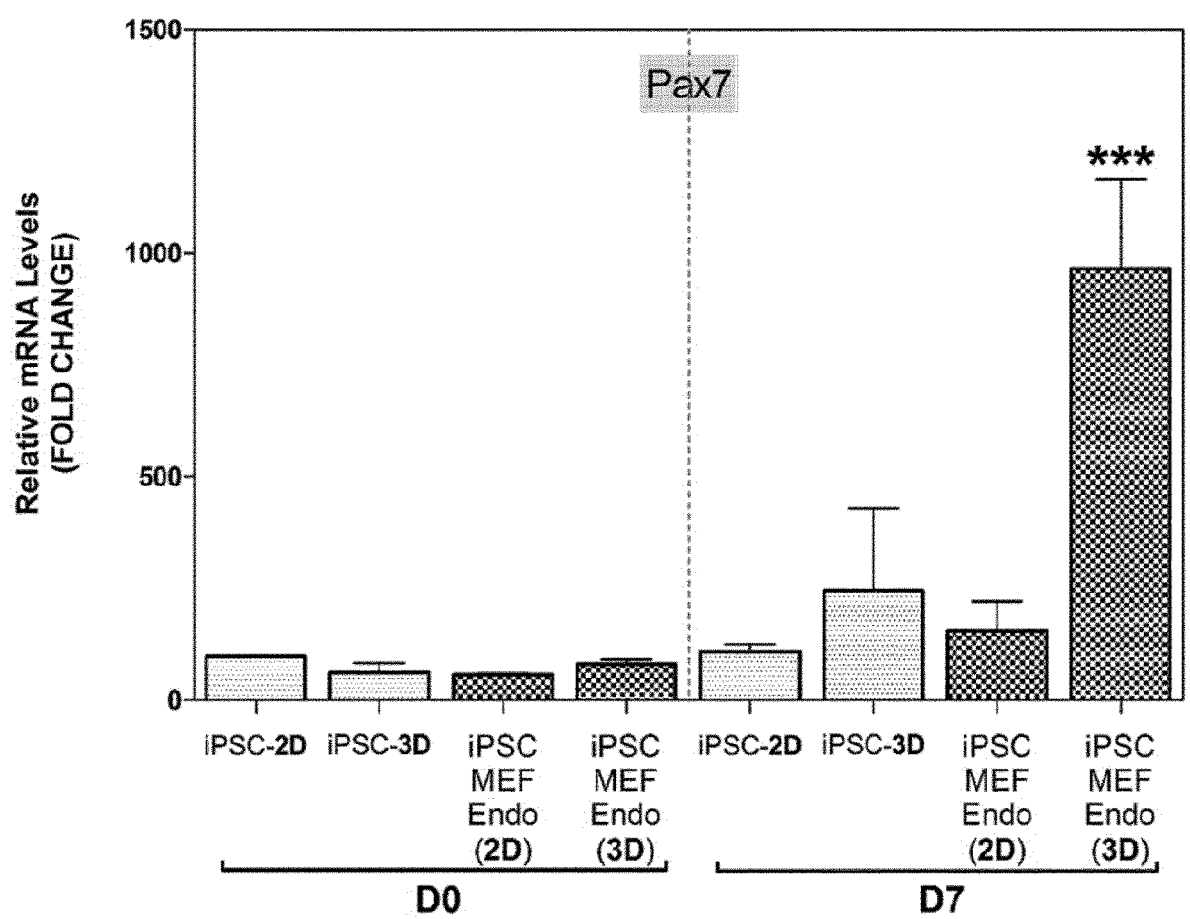

We have demonstrated that there was an advantage of using a 3-D culture system over a 2-D culture system which is evident particularly at day 7 when comparing the Pax7 expression in the triple cluster of cells (iPSC-MEF-Endo). There is a significant increase ($p \leq 0.05$) in Pax7$^+$ expression in the 3-D culture system over the 2-D culture system (FIG. 7).

Taken together we have developed a novel 3D-aggregate system for the drug-free derivation of uncommitted human MuSCs. Our protocol allows arresting myogenic lineage determination at an uncommitted state by mimicking critical niche signals. Previous published protocols lead to commitment and degeneration of pluripotent stem cell-derived MuSCs and significantly impairs their therapeutic value.

All publications mentioned in the above specification are herein incorporated by reference. Various modifications and variations of the disclosed methods, agents and uses of the invention will be apparent to the skilled person without departing from the scope and spirit of the invention. Although the invention has been disclosed in connection with specific preferred embodiments, it should be understood that the invention as claimed should not be unduly limited to such specific embodiments. Indeed, various modifications of the disclosed modes for carrying out the invention, which are obvious to the skilled person are intended to be within the scope of the following claims.

The invention claimed is:

1. A method of producing a population of muscle stem cells in vitro, the method comprising:
    admixing pluripotent stem cells, embryonic fibroblasts and endothelial cells and establishing at least one 3D spheroid comprising the pluripotent stem cells, the embryonic stem cells and the endothelial cells;
    co-culturing the pluripotent stem cells, the embryonic fibroblast cells and the endothelial cells in a 3D cell culture, wherein (a) the pluripotent stem cells and the embryonic fibroblast cells are in a ratio of about 0.3-4.1;
(b) the pluripotent stem cells and the endothelial cells are in a ratio of about 0.3-4:1; and
(c) the embryonic fibroblast cells and the endothelial cells are in a ratio of about 1-2:1; and
wherein the muscle stem cells produced are skeletal muscle stem cells.

2. The method of claim 1, wherein the pluripotent stem cells are induced pluripotent stem cells or embryonic stem cells.

3. The method of claim 1, wherein the pluripotent stem cells are human pluripotent stem cells.

4. The method of claim 1, wherein the embryonic fibroblast cells are mammalian embryonic fibroblast cells.

5. The method of claim 1, wherein the endothelial cells are mammalian endothelial cells.

6. The method of claim 1, wherein the pluripotent stem cells, the embryonic fibroblast cells and the endothelial cells are in a ratio of about 0.3-4:1:1.

7. The method of claim 1, wherein the pluripotent stem cells, the embryonic fibroblast cells and the endothelial cells are co-cultured for about 3-30 days.

8. The method of claim 1, wherein the 3D cell culture further comprises fibroblasts other than embryonic fibroblasts, smooth muscle cells and/or myoblast cells.

9. The method of claim 1, wherein the muscle stem cells are $Pax7^+$ and/or $NCAM^+$ and/or $CD82^+$.

10. The method of claim 1, wherein the muscle stem cells are negative for commitment factors.

11. The method of claim 1, wherein the pluripotent stem cells and the embryonic fibroblast cells are in a ratio of about 1.5-2.5:1.

12. The method of claim 1, wherein the pluripotent stem cells and endothelial cells are in a ratio of about 1.5-2.5:1.

13. The method of claim 1, wherein the endothelial cells are mouse or human endothelial cells.

14. The method of claim 1, wherein
(a) the pluripotent stem cells and the embryonic fibroblast cells are in a ratio of about 2:1;
(b) the pluripotent stem cells and the endothelial cells are in a ratio of about 2:1; and/or
(c) the embryonic fibroblast cells and the endothelial cells are in a ratio of about 1:1.

15. The method of claim 1, wherein the muscle stem cells are at least two selected from the group consisting of $Pax7^+$, $NCAM^+$, $CD82^+$, $GATA4^+$ and $FGF5^+$.

16. The method of claim 1, wherein the muscle stem cells are at least two selected from the group consisting of $Myf5^-$, $Myogenin^-$, $MyoD^-$ and $MYH2^-$.

* * * * *